(12) United States Patent
Lev et al.

(10) Patent No.: US 8,864,112 B2
(45) Date of Patent: Oct. 21, 2014

(54) HUMIDIFIER

(75) Inventors: Mordechai Lev, West Bloomfield, MI (US); Robert McCulloch, Macomb, MI (US); Hing Wah Tsang, Ajax (CA); Candice M. Willett, Commerce Township, MI (US)

(73) Assignee: FKA Distributing Co., LLC, Commerce Township, MI (US)

( * ) Notice: Subject to any disclaimer, the term of this patent is extended or adjusted under 35 U.S.C. 154(b) by 864 days.

(21) Appl. No.: 13/046,106

(22) Filed: Mar. 11, 2011

(65) Prior Publication Data

US 2011/0221078 A1 Sep. 15, 2011

Related U.S. Application Data

(60) Provisional application No. 61/313,420, filed on Mar. 12, 2010.

(30) Foreign Application Priority Data

Jun. 30, 2010 (CN) ............. 2010 2 0252126 U

(51) Int. Cl.
*B01F 3/04* (2006.01)

(52) U.S. Cl.
USPC 261/81; 261/142; 261/DIG. 48; 261/DIG. 89

(58) Field of Classification Search
CPC .............. A61L 9/03; A61L 9/04; C02F 1/50; C02F 1/68; C02F 2303/02; C02F 2303/04; C02F 2307/12; F24F 6/12; F24F 2003/1664; F24F 2003/1689; F24F 2006/006; F24F 2006/12

USPC ........ 261/72.1, 81, 119.1, 142, 152, DIG. 48, 261/DIG. 89

See application file for complete search history.

(56) References Cited

U.S. PATENT DOCUMENTS

| | | | | |
|---|---|---|---|---|
| 4,644,790 A | * | 2/1987 | Mizoguchi | 73/293 |
| 4,647,428 A | * | 3/1987 | Gyulay | 422/4 |
| 4,967,728 A | | 11/1990 | Dueck | |
| 5,010,905 A | * | 4/1991 | Snyder et al. | 132/272 |
| 5,278,937 A | * | 1/1994 | Alix et al. | 392/402 |
| 5,783,117 A | * | 7/1998 | Byassee et al. | 261/29 |
| 5,832,176 A | * | 11/1998 | Jung | 392/391 |
| 6,196,527 B1 | * | 3/2001 | Huang | 261/142 |
| 6,962,329 B2 | * | 11/2005 | Bachert | 261/27 |
| 7,534,406 B2 | * | 5/2009 | Takemura | 422/305 |
| 2007/0035044 A1 | * | 2/2007 | Chiu | 261/81 |
| 2007/0284765 A1 | * | 12/2007 | Wang et al. | 261/142 |
| 2010/0133162 A1 | * | 6/2010 | Huang | 210/206 |
| 2012/0112371 A1 | * | 5/2012 | Kanel et al. | 261/28 |

FOREIGN PATENT DOCUMENTS

| | | |
|---|---|---|
| CN | 201177345 | 1/2009 |
| KR | 20040034025 | 4/2004 |
| KR | 20090039262 | 4/2009 |

* cited by examiner

*Primary Examiner* — Charles Bushey
(74) *Attorney, Agent, or Firm* — Brooks Kushman P.C.

(57) ABSTRACT

A humidifier includes a main body having a hollow interior, the main body including a fluid reservoir for receiving a fluid therein, wherein the fluid reservoir is formed from a material which at least one of minimizes impurities in the fluid and militates against an emergence of impurities in the fluid, and a discharge vent coupled to the main body, wherein the discharge vent includes a removable tray for receiving a fragrance therein and a compartment for receiving a heat source therein for heating the fragrance, wherein the discharge vent emits a mist to humidify the surrounding air and an aroma of the fragrance.

20 Claims, 4 Drawing Sheets

HUMIDIFIER

CROSS-REFERENCE TO RELATED APPLICATIONS

This application claims the benefit of U.S. Provisional Patent Application Ser. No. 61/313,420 filed Mar. 12, 2010 and Chinese Utility Model Application No. 201020252126.5 filed Jun. 30, 2010, hereby incorporated herein by reference in their entirety.

FIELD OF THE INVENTION

The invention relates to a humidifier, and more particularly to a humidifier including a fluid reservoir formed from a material which at least one of minimizes an amount of impurities in a fluid contained therein and militates against an emergence of impurities in the fluid.

BACKGROUND OF THE INVENTION

A humidifier is an appliance that increases humidity (moisture) in air. Various humidifiers are commonly known in the art. One such humidifier is a water tank humidifier. The water tank humidifier includes a reservoir and an electric heater or a burner for heating water in the reservoir to produce a water vapor. Another known humidifier is a steam humidifier, which directly injects steam of high temperature and pressure into the air. A further known humidifier is an ultrasonic humidifier. The ultrasonic humidifier, typically, includes a metal diaphragm vibrating at an ultrasonic frequency to generate fine water droplets that silently exit the humidifier in the form of a cool fog. Particularly, the diaphragm creates pressure waves in the water which is gradually released from a water reservoir. The pressure waves have a desired intensity such that when the pressure waves reach a surface of the water above the diaphragm, the pressure waves expel the individual water droplets into the air, creating a water vapor. The more water vapor expelled into the air, the higher the humidity created in a surrounding area.

Unlike the water vapor generated by the humidifiers that utilize heat, the water vapor expelled by the ultrasonic humidifier may contain impurities that are present in the water such as minerals from hard water or pathogens growing in the water reservoir, for example. The minerals from the hard water may form a white dust on nearby objects. Accordingly, prior art ultrasonic humidifiers require the use of distilled water or filters to reduce the amount of impurities expelled into the air. However, an ability of the filters to remove the impurities widely varies.

Accordingly, it would be desirable to develop a humidifier including a fluid reservoir capable of at least one of minimizing an amount of impurities in a fluid contained therein and militating against an emergence of impurities in the fluid.

SUMMARY OF THE INVENTION

In concordance and agreement with the present invention a humidifier including a fluid reservoir capable of at least one of minimizing an amount of impurities in a fluid contained therein and militating against an emergence of impurities in the fluid, has surprisingly been discovered.

In one embodiment, the humidifier comprises: a main body having a hollow interior, the main body including a fluid reservoir for receiving a fluid therein, wherein the fluid reservoir is formed from a material which at least one of minimizes an amount of impurities in the fluid and militates against an emergence of impurities in the fluid; and a discharge vent coupled to the main body, wherein the discharge vent emits a mist of the fluid to humidify surrounding air.

In another embodiment, the humidifier comprises: a main body having a hollow interior, the main body including a fluid reservoir for receiving a fluid therein, wherein the fluid reservoir is formed from a material which minimizes an amount of impurities in the fluid and a microbial deterioration of the fluid reservoir, and militates against an emergence of impurities in the fluid; a diaphragm disposed in the main body, the diaphragm vibratable at an ultrasonic frequency to generate a mist; and an extensible discharge vent coupled to the main body, the discharge vent selectively positionable between a retracted position and an extended position, wherein the discharge vent emits the mist of the fluid to humidify surrounding air.

In another embodiment, the humidifier comprises: a main body having a hollow interior, the main body including a fluid reservoir for receiving a fluid therein, wherein the fluid reservoir is formed from a material which minimizes an amount of impurities in the fluid and a microbial deterioration of the fluid reservoir, and militates against an emergence of impurities in the fluid; a diaphragm disposed in the main body, the diaphragm vibratable at an ultrasonic frequency to generate a mist of the fluid; an extensible discharge vent coupled to the main body, the discharge vent including a removable tray for receiving a fragrance therein and a compartment formed adjacent the tray for receiving a heat source therein for heating the fragrance in the tray, wherein the compartment is formed to militate against heat transfer to an outer surface of the main body, and wherein the discharge vent emits the mist to humidify surrounding air; and an oscillation mechanism coupled to the discharge vent to cause an oscillation of the discharge vent when the discharge vent is in an extended position.

DESCRIPTION OF THE DRAWINGS

The above, as well as other advantages of the present invention, will become readily apparent to those skilled in the art from the following detailed description of a preferred embodiment when considered in the light of the accompanying drawings in which.

DETAILED DESCRIPTION OF EMBODIMENTS OF THE INVENTION

The following detailed description and appended drawings describe and illustrate various exemplary embodiments of the invention. The description and drawings serve to enable one skilled in the art to make and use the invention, and are not intended to limit the scope of the invention in any manner.

Figure 2:
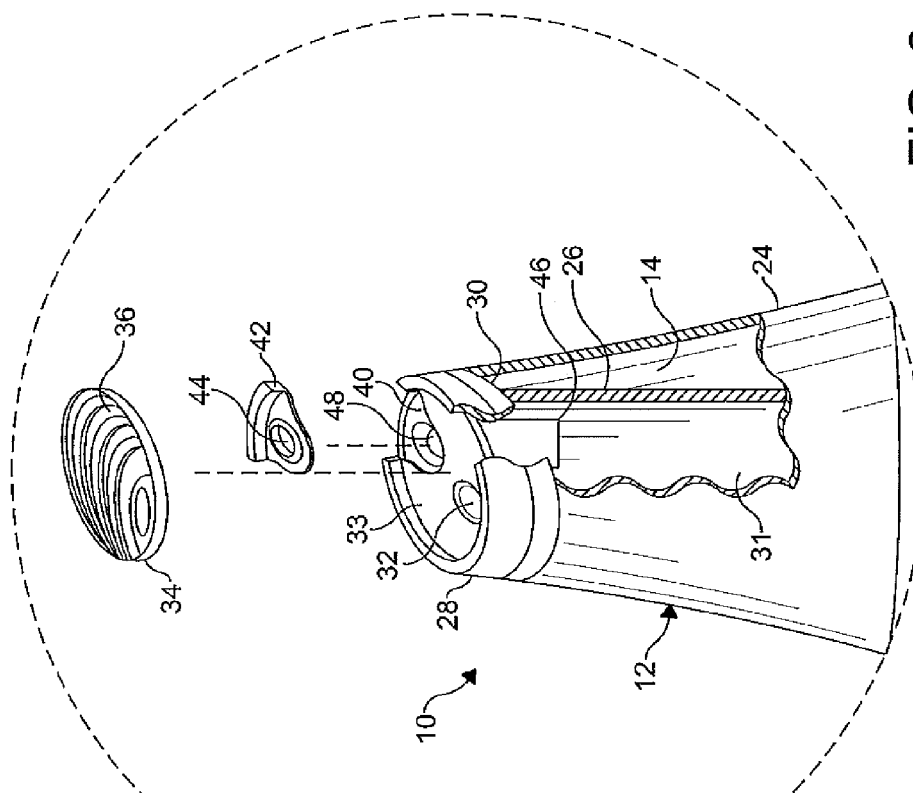
FIG. 2 is an enlarged fragmentary front perspective view of an upper portion of the humidifier illustrated in FIG. 1 within circle 2.
Figure 1:
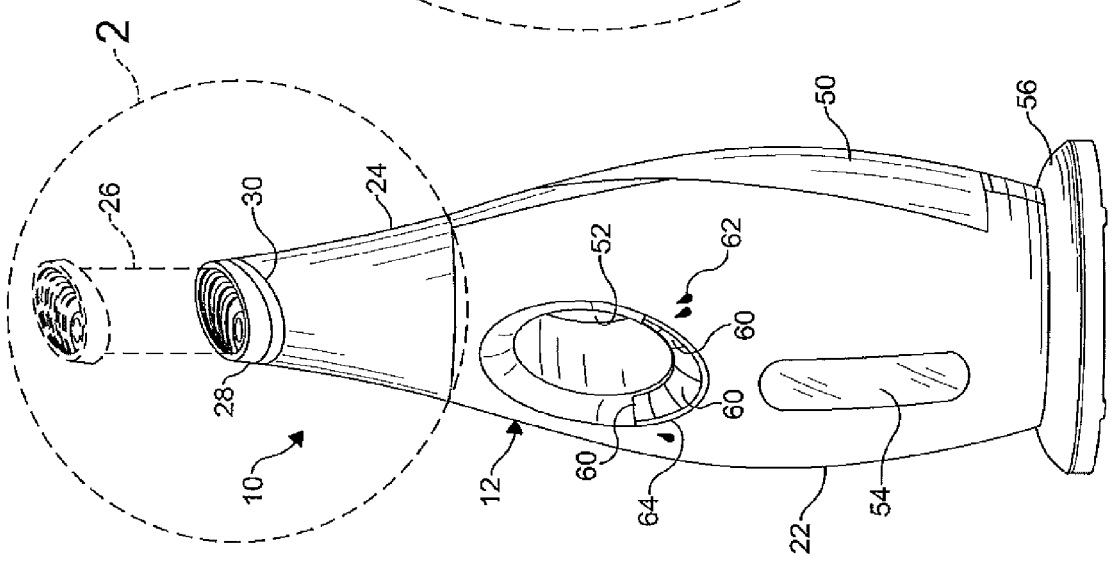
FIG. 1 is a front perspective view of a humidifier according to an embodiment of the present invention showing an extensible discharge vent in a retracted first position and an extended second position indicated by dashed lines.
Figure 3:
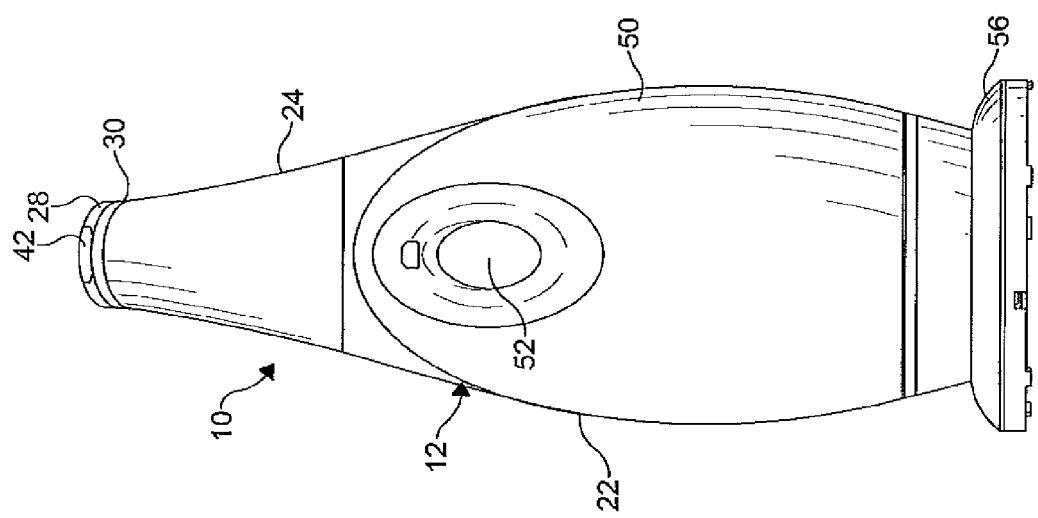
FIG. 3 is a rear elevational view of the humidifier illustrated in FIG. 1.

FIGS. 1-3 show a humidifier 10 according to an embodiment of the present invention. The humidifier 10 emits a mist such as water vapor, for example, to humidify the surrounding air. In a non-limiting example, a temperature of the mist is in a range between about 75° F. and about 90° F. In the embodiment shown, the humidifier 10 is an ultrasonic humidifier. It is understood, however, that the humidifier 10 can be any type of humidifier as desired such as a water tank humidifier or a steam humidifier, for example. The humidifier 10 includes a main body 12 having a hollow interior 14. Components (not shown) and devices (not shown) necessary for operation and control of the humidifier 10 such as a diaphragm capable of vibrating at an ultrasonic frequency, a motor, electrical wiring, a heater for heating the mist, an oscillation mechanism, and the like, for example, are received in the hollow interior 14. The main body 12 is formed from any suitable material such as a plastic material, for example.

As illustrated in FIG. 1, the main body 12 includes an extensible discharge vent 24. The discharge vent 24 is selectively positionable between a retracted first position and an extended second position as indicated by dashed lines. The discharge vent 24 includes a neck portion 26 having a spout 28 formed thereon. In the first position of the discharge vent 24, the neck portion 26 is received in the hollow interior 14 of the main body 12 and the spout 28 seats on an annular collar 30 thereof. In the second position of the discharge vent 24, the neck portion 26 extends laterally outwardly from the main body 12. Additionally, in the second position, the discharge vent 24 may be caused to oscillate by the oscillation mechanism or rotate to increase an area of the surrounding air into which the mist from the humidifier 10 is emitted. It is understood that the oscillation mechanism can be activated automatically when the neck portion 26 is extended or manually by a user, for example. As shown in FIG. 2, the neck portion 26 includes a passageway 31 formed therein. The passageway 31 is in fluid communication with the hollow interior 14 of the main body 12 and a discharge outlet 32 formed in the spout 28. The main body 12 may further include a fan (not shown) to cause the mist to travel through the passageway 31 of the discharge vent 24.

The spout 28 includes a recess 33 formed therein. The recess 33 receives a cover 34 having slotted openings 36 formed therein. It is understood that the openings 36 can have any shape and size as desired. The cover 34 disperses fluid droplets in the mist emitted from the humidifier 10. An indentation 40 is formed in the spout 28 to receive a removable tray 42 therein. It is understood that the tray 42 can be produced from any suitable material such as a washable (e.g. dishwasher safe), plastic material, for example. The tray 42 includes a cavity 44 formed therein. The cavity 44 receives a fragrance (not shown) therein for emitting an aroma into the surrounding air. It is understood that the fragrance can be any fragrance as desired such as a liquid or gel fragrance which emits an aroma when heated, for example.

The discharge vent 24 further includes a compartment 46 formed therein. As illustrated, the compartment 46 is formed adjacent the cavity 44 of the tray 42 and is accessible to the user when the tray 42 is removed from the spout 28. It is understood that the compartment 46 can be formed elsewhere in the main body 12 of the humidifier 10 if desired. The compartment 46 receives a heat source 48 therein such as a light bulb, for example, to facilitate a heating of the fragrance in the tray 42. The compartment 46 is formed to militate against a transfer of heat to an outer surface of the main body 12 such as forming the compartment 46 from an insulating material or providing the compartment 46 with reflective walls to cause a transfer of heat to the tray 42, for example.

As shown in FIG. 1, the main body 12 further includes a fluid reservoir 50. The fluid reservoir 50 is received in a cavity (not shown) formed in the main body 12. The fluid reservoir 50 is positionable between an open position and a closed position as illustrated. The fluid reservoir 50 receives a fluid (not shown) therein such as water, for example. It is understood that the fluid reservoir 50 has a predetermined fluid capacity. In a non-limiting example, the predetermined fluid capacity is in a range of about 0.1 gallon to about 3 gallons. In another non-limiting example, the predetermined fluid capacity is about 1.5 gallons. The fluid reservoir 50 is formed from a material which minimizes microbial deterioration of the fluid reservoir 50 and minimizes an amount of and militates against an emergence of impurities such as minerals and pathogens, for example, in the fluid contained therein. In a non-limiting example, the fluid reservoir 50 is formed from a plastic resin material including an antimicrobial additive (e.g. Vinyzene™ SB-1). It is understood, however, that the fluid reservoir 50 can be formed any suitable material. An opening 52 is formed through the main body 12, including the fluid reservoir 50. As shown, the opening 52 extends from a front of the humidifier 10 to a rear thereof. It is understood that the opening 52 can be formed elsewhere in the main body 12 if desired. The opening 52 can be sized to receive at least a portion of a hand of the user, thereby permitting the user to grasp at least a portion of the main body 12 to transport the humidifier 10 or at least a portion of the fluid reservoir 50 to position the fluid reservoir 50 between the open and closed positions.

The main body 12 may further include a fluid level indicator 54. The indicator 54 permits the user to monitor a fluid level in the fluid reservoir 50 and determine when the fluid reservoir 50 needs to be refilled. In the embodiment shown, the indicator 54 is a substantially transparent or translucent portion of the main body 12. It is understood that the indicator 54 can be any indicator as desired such as an opening formed in the main body 12 provided with a substantially transparent or translucent cover, for example.

A base 56 may be provided on the main body 12. The base 56 supports the main body 12, permitting the humidifier 10 to be placed on a substantially planar surface such as a floor, a counter top, or a desktop, for example. It is understood that the base 56 can have any shape and size as desired. The main body 12 may also include human interfaces 60 necessary for operation and control of the humidifier 10. In the embodiment shown, the human interfaces 60 are for activating and deactivating the humidifier 10, the heat source 48, the oscillation mechanism, and the heater for heating the mist, and for increasing and decreasing a volume of the mist emitted from the humidifier 10. Additional or fewer human interfaces 60 than shown for operating and controlling other components, devices, and features of the humidifier 10 can be employed if desired. It is understood that the human interfaces 60 can be located anywhere on the humidifier 10 as desired. It is further understood that the human interfaces 60 can be any human interfaces 60 such as a push button, a rotatable knob, a slide, a toggle switch, and the like, for example.

The main body 12 may also be provided with indicia 62 (e.g. a fluid droplet symbol) or a light source 64 (e.g. a light emitting diode) for indicating various operations of the humidifier 10 such as a volume level of the mist emitted from the humidifier 10 or activation of the humidifier 10, for example. As illustrated in FIG. 1, the volume level of the mist emitted from the humidifier 10 ranges between a minimum level indicated by one indicia 62 and a maximum level indicated by two indicia 62.

In operation, at least a portion of the hand of the user is received into the opening 52 formed in the main body 12 to permit the user to grasp a portion of the fluid reservoir 50 and position the fluid reservoir 50 in the open position. The fluid reservoir 50 is then filled with the fluid. Thereafter, using the opening 52, the user grasps a portion of the fluid reservoir 50 and positions the fluid reservoir 50 in the closed position. While the fluid is the fluid reservoir 50, the antimicrobial additive in the material used to form the fluid reservoir 50 minimizes microbial deterioration of the fluid reservoir 50 caused by the impurities and minimizes the amount of and militates against the emergence of the impurities in the fluid. Particularly, in a non-limiting example, molecules of the antimicrobial additive in the material used to form the fluid reservoir 50 migrate, overtime, from a molecular substrate of the material and onto a surface thereof to form an antimicrobial film thereon. The migration of the antimicrobial molecules is driven by inherent compatibility differences between the antimicrobial molecules and the substrate of the material. The antimicrobial molecules of the antimicrobial film interact with the fluid in the fluid reservoir 50 to minimize the amount of and militate against the emergence of the impurities in the fluid. The antimicrobial film on the surface of the material is replenished by the migration of additional molecules from the substrate.

An initial actuation of one of the human interfaces 60 by the user causes the humidifier 10 to activate. Particularly, the diaphragm disposed in the hollow interior 14 of the main body 12 is caused to vibrate at an ultrasonic frequency. The vibration of the diaphragm generates pressure waves in the fluid gradually released from the fluid reservoir 50. The pressure waves have a desired intensity such that when the pressure waves reach a surface of the fluid above the diaphragm, the pressure waves expel the fluid droplets, creating a mist. The temperature of the mist generated by the pressure waves is cool. To heat the mist, the user activates the heater for heating the mist by actuating one of the human interfaces 62. Alternatively, the heater for heating the mist is automatically activated and the temperature of the mist is warm. Accordingly, to generate a cool mist, the user deactivates the heater for heating the mist by actuating one of the human interfaces 62.

The mist travels through the main body 12 of the humidifier 10, into and through the passageway 31 of the discharge vent 24, and through the discharge outlet 32. The cover 34 disperses the fluid droplets of the mist to humidify the surrounding air. When the user desires a concentrated dispersion of the mist, the discharge vent 24 is positioned in the first position. When the user desires to increase the area of the surrounding air into which the mist is emitted, the discharge vent 24 is positioned in the second position as indicated by the dashed lines in FIG. 1. A subsequent actuation of one of the human interfaces 60 by the user causes the humidifier 10 to deactivate. The user monitors the fluid level indicator 54 to determine when the fluid reservoir 50 needs to be refilled.

The user may also actuate other human interfaces 60 to control the volume of the mist emitted from the humidifier 10, and activate and deactivate other features of the humidifier 10 such as the heat source 48 for heating the fragrance in the tray 42, the oscillation mechanism for causing the discharge vent 24 to oscillate, and the heater for heating the mist, for example.

To fill, remove, or replace the fragrance in the cavity 44 of the tray 42, the cover 34 is separated from the spout 28 of the discharge vent. Once the fragrance is filled, removed, or replaced, the user replaces the cover 34 by inserting the cover 34 into the recess 33 formed in the spout 28.

To insert, remove, or replace the heat source 48 in the compartment 46, the cover 34 and tray 42 are separated from the spout 28 of the discharge vent 24. After the heat source 48 is inserted, removed, or replaced, the tray 42 is placed in the indentation 40 of the spout 28 and the cover 34 is placed in the recess 33 thereof.

FIGS. 4-5 show a humidifier 100 according to an embodiment of the present invention. The humidifier 100 emits a mist such as water vapor, for example, to humidify the surrounding air. In the embodiment shown, the humidifier 100 is an ultrasonic humidifier. It is understood, however, that the humidifier 100 can be any type of humidifier as desired such as a water tank humidifier or a steam humidifier, for example. The humidifier 100 includes a main body 112 having a hollow interior 114. Components (not shown) and devices (not shown) necessary for operation and control of the humidifier 100 such as a diaphragm capable of vibrating at an ultrasonic frequency, a motor, electrical wiring, a heater for heating the mist, an oscillation mechanism, and the like, for example, are received in the hollow interior 114. The main body 112 is formed from any suitable material such as a plastic material, for example.

As illustrated in FIG. 4, the main body 114 includes an extensible discharge vent 124 removeably coupled thereto. The discharge vent 124 is selectively positionable between a retracted first position and an extended second position as indicated by dashed lines. The discharge vent 124 includes a neck portion 126 having a spout 128 formed thereon. In the first position of the discharge vent 124, the neck portion 126 is received in the hollow interior 114 of the main body 112 and the spout 128 seats on an annular collar 130 thereof. In the second position of the discharge vent 124, the neck portion 126 extends laterally outwardly from the main body 112. Additionally, in the second position, the discharge vent 124 may be caused to oscillate by the oscillation mechanism or rotate to increase an area of the surrounding air into which the mist from the humidifier 100 is emitted. It is understood that the oscillation mechanism can be activated automatically when the neck portion 126 is extended or manually by a user, for example. As shown in FIG. 5, the neck portion 126 includes a passageway 131 formed therein. The passageway 131 is in fluid communication with the hollow interior 114 of the main body 112 and a discharge outlet 132 formed in the spout 128. The main body 112 may further include a fan (not shown) to cause the mist to travel through the passageway 131 of the discharge vent 124.

The spout 128 includes a recess 133 formed therein. The recess 133 receives a cover 134 having slotted openings 136 formed therein. It is understood that the openings 136 can have any shape and size as desired. The cover 134 disperses fluid droplets in the mist emitted from the humidifier 100. An indentation 140 is formed in the spout 128 to receive a removable tray 142 therein. It is understood that the tray 142 can be produced from any suitable material such as a washable (e.g. dishwasher safe), plastic material, for example. The tray 142 includes a cavity 144 formed therein. The cavity 144 receives a fragrance (not shown) therein for emitting an aroma into the surrounding air. It is understood that the fragrance can be any fragrance as desired such as a liquid or gel fragrance which emits an aroma when heated, for example.

The discharge vent 124 further includes a compartment 146 formed therein. As illustrated, the compartment 146 is formed adjacent the cavity 144 of the tray 142 and is accessible to the user when the tray 142 is removed from the spout 128. It is understood that the compartment 146 can be formed elsewhere in the main body 112 of the humidifier 100 if desired. The compartment 146 receives a heat source 148 therein such as a light bulb, for example, to facilitate a heating of the fragrance in the tray 142. The compartment 146 is formed to militate against a transfer of heat to an outer surface of the main body 112 such as forming the compartment 146 from an insulating material or providing the compartment 146 with reflective walls to cause a transfer of heat to the tray 142, for example.

The main body 112 further includes a fluid reservoir 150. The fluid reservoir 150 receives a fluid (not shown) therein such as water, for example. It is understood that the fluid reservoir 150 has a predetermined fluid capacity. In a non-limiting example, the predetermined fluid capacity is in a range of about 0.1 gallon to about 3 gallons. In another non-limiting example, the predetermined fluid capacity is about 1 gallon. The fluid reservoir 150 is formed from a material which minimizes microbial deterioration of the fluid reservoir 150 and minimizes an amount of and militates against an emergence of impurities such as minerals and pathogens, for example, in the fluid contained therein. In a non-limiting example, the fluid reservoir 150 is formed from a plastic resin material including an antimicrobial additive (e.g. Vinyzene™ SB-1). It is understood, however, that the fluid reservoir 150 can be formed any suitable material. A mouth (not shown) is formed in the fluid reservoir 150 to permit the user to fill the fluid reservoir 150 with the fluid. The mouth is accessible to the user when the discharge vent 124 is separated from the main body 112.

Figure 4:
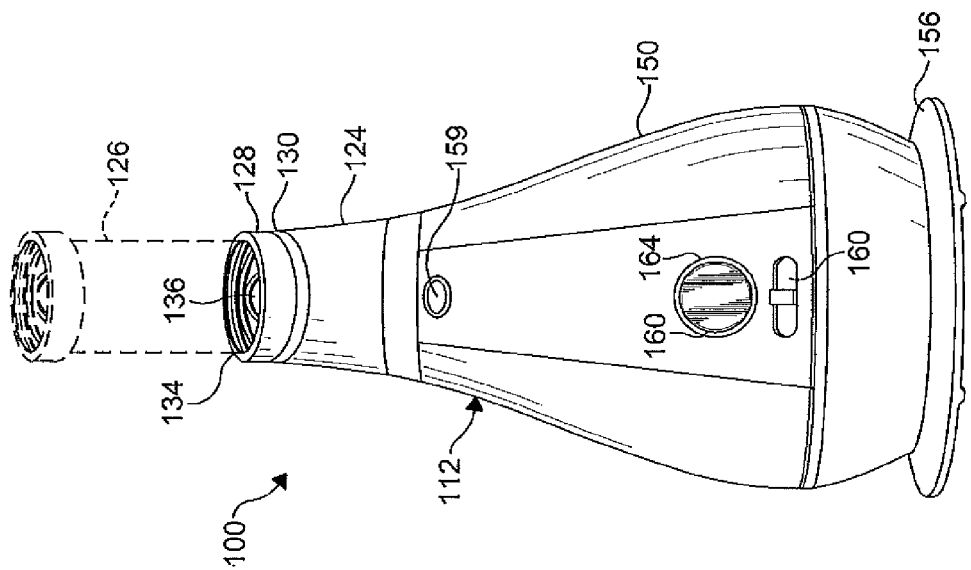
FIG. 4 is a front elevational view of a humidifier according to another embodiment of the invention showing an extensible discharge vent in a retracted first position and an extended second position indicated by dashed lines.

A base 156 may be provided on the main body 112. The base 156 supports the main body 112, permitting the humidifier 100 to be placed on a substantially planar surface such as a floor, a counter top, or a desktop, for example. It is understood that the base 156 can have any shape and size as desired. As shown, the main body 112 is provided with a releasable handle 157. It is understood that the handle 157 can be disposed elsewhere on the main body 112 if desired. The handle 157 may be used to transport the humidifier 100 or to separate the fluid reservoir 150 from the base 156 for refilling the fluid reservoir 150. An indentation 158, sized to receive a finger of the user, may be used to pull the handle 157 laterally outwardly from the main body 112 and release the handle 157 from the fluid reservoir 150. Alternatively, the main body 112 may include a release button 159, as shown in FIG. 4, to release the handle 157 and the fluid reservoir 150 from a locked position in the base 156. It is understood that the release button 159 can be located anywhere on the main body 112 as desired.

As illustrated in FIG. 4, the main body 112 may also include human interfaces 160 necessary for operation and control of the humidifier 100. In the embodiment shown, the human interfaces 160 are for activating and deactivating the humidifier 100 and the heat source 148. It is understood that the human interfaces 160 can be used for operating and controlling other components, devices, and features of the humidifier 100 such as activating and deactivating the oscillation mechanism and the heater for heating the mist, and for increasing and decreasing a volume of the mist emitted from the humidifier 100, for example. Additional or fewer human interfaces 160 than shown for operating and controlling other components, devices, and features of the humidifier 100 can be employed if desired. It is understood that the human interfaces 160 can be located anywhere on the humidifier 100 as desired. It is further understood that the human interfaces 160 can be any human interfaces 160 such as a push button, a rotatable knob, a slide, a toggle switch, and the like, for example. The main body 112 may also include indicia (not shown) or a light source 164 such as a light emitting diode (LED) for indicating activation of the humidifier 100, for example.

The main body 112 may further include a fluid level indicator (not shown). The indicator permits the user to monitor a fluid level in the fluid reservoir 150 and determine when the fluid reservoir 150 needs to be refilled. It is understood that the indicator can be any indicator as desired such as an opening formed in the main body 112 provided with a substantially transparent or translucent cover, for example.

In operation, the user separates the discharge vent 124 from the main body 112, thereby providing access to the mouth of the fluid reservoir 150. The fluid reservoir 150 is then filled with the fluid. The discharge vent 124 is then placed on the main body 112 and removeably coupled thereto. While the fluid is the fluid reservoir 150, the antimicrobial additive in the material used to form the fluid reservoir 150 minimizes microbial deterioration of the fluid reservoir 150 caused by the impurities and minimizes the amount of and militates against the emergence of the impurities in the fluid. Particularly, in a non-limiting example, molecules of the antimicrobial additive in the material used to form the fluid reservoir 150 migrate, overtime, from a molecular substrate of the material and onto a surface thereof to form an antimicrobial film thereon. The migration of the antimicrobial molecules is driven by inherent compatibility differences between the antimicrobial molecules and the substrate of the material. The antimicrobial molecules of the antimicrobial film interact with the fluid in the fluid reservoir 150 to minimize the amount of and militate against the emergence of the impurities in the fluid. The antimicrobial film on the surface of the material is replenished by the migration of additional molecules from the substrate.

An initial actuation of one of the human interfaces 160 by the user causes the humidifier 100 to activate. Particularly, the diaphragm disposed in the hollow interior 114 of the main body 112 is caused to vibrate at an ultrasonic frequency. The vibration of the diaphragm generates pressure waves in the fluid gradually released from the fluid reservoir 150. The pressure waves have a desired intensity such that when the pressure waves reach a surface of the fluid above the diaphragm, the pressure waves expel the fluid droplets, creating a mist. The mist travels through the main body 112 of the humidifier 100, into and through the passageway 131 of the discharge vent 124, and through the discharge outlet 132. The cover 134 disperses the fluid droplets of the mist to humidify the surrounding air. When the user desires a concentrated dispersion of the mist, the discharge vent 124 is positioned in the first position. When the user desires to increase the area of the surrounding air into which the mist is emitted, the discharge vent 124 is positioned in the second position as indicated by the dashed lines in FIG. 4. A subsequent actuation of one of the human interfaces 160 by the user causes the humidifier 100 to deactivate. The user monitors the fluid level indicator to determine when the fluid reservoir 150 needs to be refilled.

The user may also actuate other human interfaces 160 to control the volume of the mist emitted from the humidifier 100, and activate and deactivate other features of the humidifier 10 such as the heat source 148 for heating the fragrance in the tray 142, the oscillation mechanism for causing the discharge vent 124 to oscillate, and the heater for heating the mist, for example.

To fill, remove, or replace the fragrance in the cavity 144 of the tray 142, the cover 134 is separated from the spout 128 of the discharge vent 123. Once the fragrance is filled, removed, or replaced, the cover 134 is placed and secured in the recess 133 thereof.

To insert, remove, or replace the heat source 148 in the compartment 146, the cover 134 and tray 142 are separated from the spout 128 of the discharge vent 124. After the heat source 148 is inserted, removed, or replaced, the tray 142 is placed in the indentation 140 of the spout 128 and the cover 134 is placed and secured in the recess 133 thereof.

Figure 6:
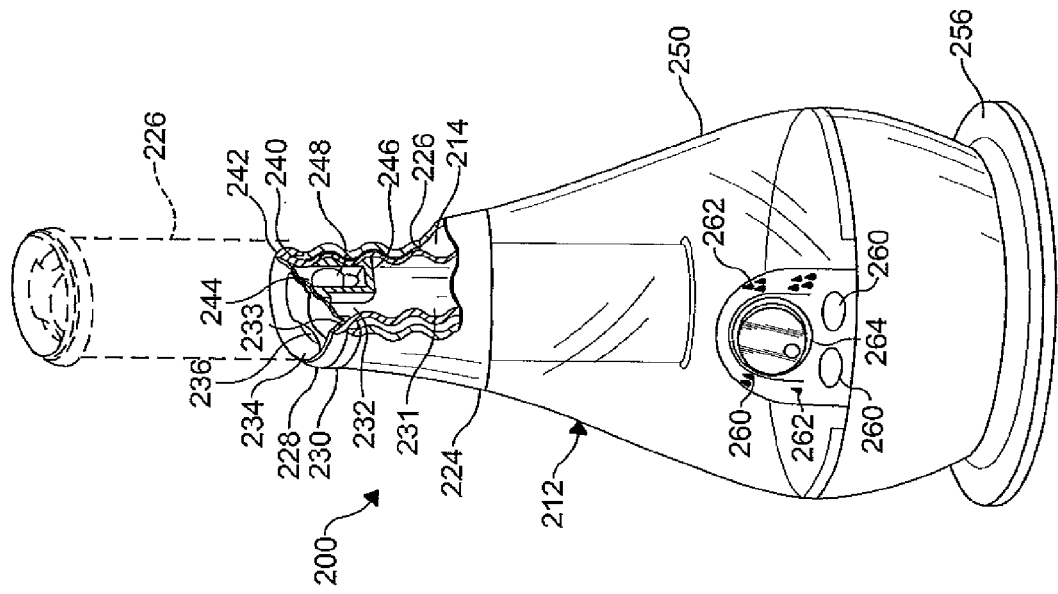
FIG. 6 is a front perspective view of a humidifier according to another embodiment of the invention showing an extensible discharge vent in a retracted first position and an extended second position indicated by dashed lines and showing a portion of the humidifier cut away.
Figure 5:
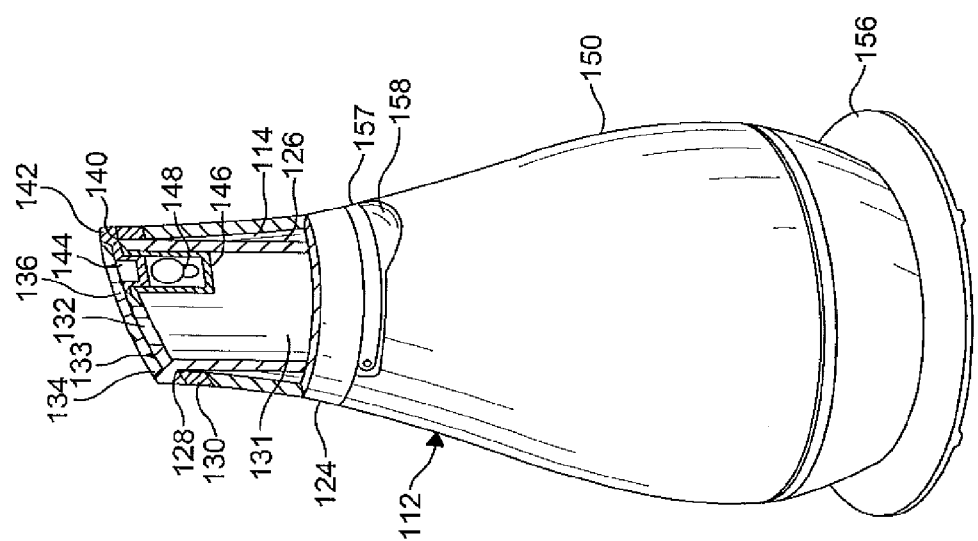
FIG. 5 is a rear perspective view of the humidifier illustrated in FIG. 4 showing a portion thereof in section.

FIG. 6 shows a humidifier 200 according to an embodiment of the present invention. The humidifier 200 emits a mist such as water vapor, for example, to humidify the surrounding air. In the embodiment shown, the humidifier 200 is an ultrasonic humidifier. It is understood, however, that the humidifier 200 can be any type of humidifier as desired such as a water tank humidifier or a steam humidifier, for example. The humidifier 200 includes a main body 212 having a hollow interior 214. Components (not shown) and devices (not shown) necessary for operation and control of the humidifier 200 such as a diaphragm capable of vibrating at an ultrasonic frequency, a motor, electrical wiring, a heater for heating the mist, an oscillation mechanism, and the like, for example, are received in the hollow interior 214. The main body 212 is formed from any suitable material such as a plastic material, for example.

As illustrated, the main body 214 includes an extensible discharge vent 224 removeably coupled thereto. The discharge vent 224 is selectively positionable between a retracted first position and an extended second position as indicated by dashed lines. The discharge vent 224 includes a neck portion 226 having a spout 228 formed thereon. In the first position of the discharge vent 224, the neck portion 226 is received in the hollow interior 214 of the main body 212 and the spout 228 seats on an annular collar 230 thereof. In the second position of the discharge vent 224, the neck portion 226 extends laterally outwardly from the main body 212. Additionally, in the second position, the discharge vent 224 may be caused to oscillate by the oscillation mechanism or rotate to increase an area of the surrounding air into which the mist from the humidifier 200 is emitted. It is understood that the oscillation mechanism can be activated automatically when the neck portion 226 is extended or manually by a user, for example. The neck portion 226 includes a passageway 231 formed therein. The passageway 231 is in fluid communication with the hollow interior 214 of the main body 212 and a discharge outlet 232 formed in the spout 228. The main body 212 may further include a fan (not shown) to cause the mist to travel through the passageway 231 of the discharge vent 224.

As shown, the spout 228 includes a recess 233 formed therein. The recess 233 receives a cover 234 having openings 236 formed therein. It is understood that the openings 236 can have any shape and size as desired. The cover 234 disperses fluid droplets in the mist emitted from the humidifier 200. An indentation 240 is formed in the spout 228 to receive a removable tray 242 therein. It is understood that the tray 242 can be produced from any suitable material such as a washable (e.g. dishwasher safe), plastic material, for example. The tray 242 includes a cavity 244 formed therein. The cavity 244 receives a fragrance (not shown) therein for emitting an aroma into the surrounding air. It is understood that the fragrance can be any fragrance as desired such as a liquid or gel fragrance which emits an aroma when heated, for example.

The discharge vent 224 further includes a compartment 246 formed therein. As illustrated, the compartment 246 is formed adjacent the cavity 244 of the tray 242 and is accessible to the user when the tray 242 is removed from the spout 228. It is understood that the compartment 246 can be formed elsewhere in the main body 212 of the humidifier 200 if desired. The compartment 246 receives a heat source 248 therein such as a light bulb, for example, to facilitate a heating of the fragrance in the tray 242. The compartment 246 is formed to militate against a transfer of heat to an outer surface of the main body 212 such as forming the compartment 246 from an insulating material or providing the compartment 246 with reflective walls to cause a transfer of heat to the tray 242, for example.

The main body 212 further includes a fluid reservoir 250. The fluid reservoir 250 receives a fluid (not shown) therein such as water, for example. It is understood that the fluid reservoir 250 has a predetermined fluid capacity. In a non-limiting example, the predetermined fluid capacity is in a range of about 0.1 gallon to about 3 gallons. In another non-limiting example, the predetermined fluid capacity is about 1 gallon. The fluid reservoir 250 is formed from a material which minimizes microbial deterioration of the fluid reservoir 250 and minimizes an amount of and militates against an emergence of impurities such as minerals and pathogens, for example, in the fluid contained therein. In a non-limiting example, the fluid reservoir 250 is formed from a substantially translucent or transparent plastic resin material including an antimicrobial additive (e.g. Vinyzene™ SB-1). It is understood, however, that the fluid reservoir 250 can be formed any suitable material. A mouth (not shown) is formed in the fluid reservoir 250 to permit the user to fill the fluid reservoir 250 with the fluid. The mouth is accessible to the user when the discharge vent 224 is separated from the main body 212. In the embodiment shown, the fluid reservoir 250 may further include a light source (not shown) disposed therein. The light source illuminates the fluid reservoir 250, causing the fluid reservoir 250 to emit light therefrom. In a non-limiting example, the humidifier 200 including the light source acts as a night light.

A base 256 may be provided on the main body 212. The base 256 supports the main body 212, permitting the humidifier 200 to be placed on a substantially planar surface such as a floor, a counter top, or a desktop, for example. It is understood that the base 256 can have any shape and size as desired. The main body 212 may also include human interfaces 260 necessary for operation and control of the humidifier 200. In the embodiment shown, the human interfaces 260 are for activating and deactivating the humidifier 200, the heat source 248, and the light source, and for increasing and decreasing a volume of the mist emitted from the humidifier 200. It is understood that the human interfaces 260 can be used for operating and controlling other components, devices, and features of the humidifier 200 such as activating and deactivating the oscillation mechanism, the heater for heating the mist, and the like, for example. Additional or fewer human interfaces 260 than shown for operating and controlling other components, devices, and features of the humidifier 200 can be employed if desired. It is understood that the human interfaces 260 can be located anywhere on the humidifier 200 as desired. It is further understood that the human interfaces 260 can be any human interfaces 260 such as a push button, a rotatable knob, a slide, a toggle switch, and the like, for example.

The main body 212 may also include indicia 262 (e.g. a fluid droplet symbol) or a light source 264 (e.g. a light emitting diode) for indicating a volume level of the mist emitted from the humidifier 200 or activation of the humidifier 200, for example. As illustrated in FIG. 6, the volume level of the mist emitted from the humidifier 200 ranges between a low level indicated by one indicia 262, a medium level indicated by two indicia 262, a medium-high level indicated by three indicia 262, and a maximum level indicated by four indicia 262.

In operation, the user separates the discharge vent 224 from the main body 212, thereby providing access to the mouth of the fluid reservoir 250. The fluid reservoir 250 is then filled with the fluid. The discharge vent 224 is then placed on the main body 212 and removeably coupled thereto. While the fluid is the fluid reservoir 250, the antimicrobial additive in the material used to form the fluid reservoir 250 minimizes microbial deterioration of the fluid reservoir 250 caused by the impurities and minimizes the amount of and militates against the emergence of the impurities in the fluid. Particularly, in a non-limiting example, molecules of the antimicrobial additive in the material used to form the fluid reservoir 250 migrate, overtime, from a molecular substrate of the material and onto a surface thereof to form an antimicrobial film thereon. The migration of the antimicrobial molecules is driven by inherent compatibility differences between the antimicrobial molecules and the substrate of the material. The antimicrobial molecules of the antimicrobial film interact with the fluid in the fluid reservoir 250 to minimize the amount of and militate against the emergence of the impurities in the fluid. The antimicrobial film on the surface of the material is replenished by the migration of additional molecules from the substrate.

An initial actuation of one of the human interfaces 260 by the user causes the humidifier 200 to activate. Particularly, the diaphragm disposed in the hollow interior 214 of the main body 212 is caused to vibrate at an ultrasonic frequency. The vibration of the diaphragm generates pressure waves in the fluid gradually released from the fluid reservoir 250. The pressure waves have a desired intensity such that when the pressure waves reach a surface of the fluid above the diaphragm, the pressure waves expel the fluid droplets, creating a mist. The mist travels through the main body 212 of the humidifier 200, into and through the passageway 231 of the discharge vent 224, and through the discharge outlet 232. The cover 234 disperses the fluid droplets of the mist to humidify the surrounding air. When the user desires a concentrated dispersion of the mist, the discharge vent 224 is positioned in the first position. When the user desires to increase the area of the surrounding air into which the mist is emitted, the discharge vent 224 is positioned in the second position as indicated by the dashed lines in FIG. 6. A subsequent actuation of one of the human interfaces 260 by the user causes the humidifier 200 to deactivate.

The user may also actuate other human interfaces 260 to control the volume of the mist emitted from the humidifier 200, and activate and deactivate other features of the humidifier 200 such as the heat source 248 for heating the fragrance in the tray 242, the light source for illuminating the fluid reservoir 250, the oscillation mechanism for causing the discharge vent 224 to oscillate, and the heater for heating the mist, for example.

To fill, remove, or replace the fragrance in the cavity 244 of the tray 242, the cover 234 is separated from the spout 228 of the discharge vent 223. Once the fragrance is filled, removed, or replaced, the cover 234 is placed and secured in the recess 233 thereof.

To insert, remove, or replace the heat source 248 in the compartment 246, the cover 234 and tray 242 are separated from the spout 228 of the discharge vent 224. After the heat source 248 is inserted, removed, or replaced, the tray 242 is placed in the indentation 240 of the spout 228 and the cover 234 is placed and secured in the recess 233 thereof.

Figure 7:
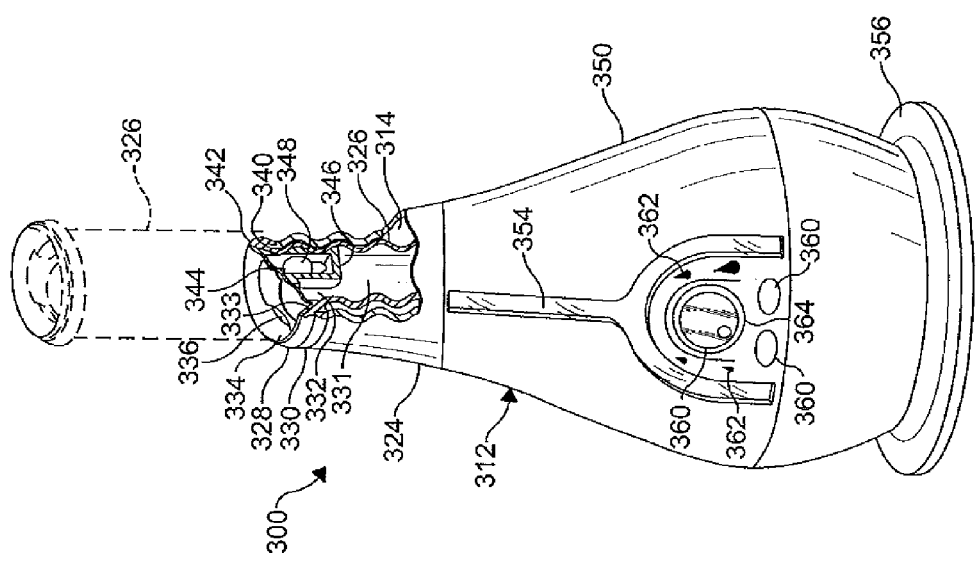
FIG. 7 is a front perspective view of a humidifier according to another embodiment of the invention showing an extensible discharge vent in a retracted first position and an extended second position indicated by dashed lines and showing a portion of the humidifier cut away.

FIG. 7 shows a humidifier 300 according to an embodiment of the present invention. The humidifier 300 emits a mist such as water vapor, for example, to humidify the surrounding air. In the embodiment shown, the humidifier 300 is an ultrasonic humidifier. It is understood, however, that the humidifier 300 can be any type of humidifier as desired such as a water tank humidifier or a steam humidifier, for example. The humidifier 300 includes a main body 312 having a hollow interior 314. Components (not shown) and devices (not shown) necessary for operation and control of the humidifier 300 such as a diaphragm capable of vibrating at an ultrasonic frequency, a motor, electrical wiring, a heater for heating the mist, an oscillation mechanism, and the like, for example, are received in the hollow interior 314. The main body 312 is formed from any suitable material such as a plastic material, for example.

As illustrated, the main body 314 includes an extensible discharge vent 324 removeably coupled thereto. The discharge vent 324 is selectively positionable between a retracted first position and an extended second position as indicated by dashed lines. The discharge vent 324 includes a neck portion 326 having a spout 328 formed thereon. In the first position of the discharge vent 324, the neck portion 326 is received in the hollow interior 314 of the main body 312 and the spout 328 seats on an annular collar 330 thereof. In the second position of the discharge vent 324, the neck portion 326 extends laterally outwardly from the main body 312. Additionally, in the second position, the discharge vent 324 may be caused to oscillate by the oscillation mechanism or rotate to increase an area of the surrounding air into which the mist from the humidifier 300 is emitted. It is understood that the oscillation mechanism can be activated automatically when the neck portion 326 is extended or manually by a user, for example. The neck portion 326 includes a passageway 331 formed therein. The passageway 331 is in fluid communication with the hollow interior 314 of the main body 312 and a discharge outlet 332 formed in the spout 328. The main body 312 may further include a fan (not shown) to cause the mist to travel through the passageway 331 of the discharge vent 324.

As shown, the spout 328 includes a recess 333 formed therein. The recess 333 receives a cover 334 having openings 336 formed therein. It is understood that the openings 336 can have any shape and size as desired. The cover 334 disperses fluid droplets in the mist emitted from the humidifier 300. An indentation 340 is formed in the spout 328 to receive a removable tray 342 therein. It is understood that the tray 342 can be produced from any suitable material such as a washable (e.g. dishwasher safe), plastic material, for example. The tray 342 includes a cavity 344 formed therein. The cavity 344 receives a fragrance (not shown) therein for emitting an aroma into the surrounding air. It is understood that the fragrance can be any fragrance as desired such as a liquid or gel fragrance which emits an aroma when heated, for example.

The discharge vent 324 further includes a compartment 346 formed therein. As illustrated, the compartment 346 is formed adjacent the cavity 344 of the tray 342 and is accessible to the user when the tray 342 is removed from the spout 328. It is understood that the compartment 346 can be formed elsewhere in the main body 312 of the humidifier 300 if desired. The compartment 346 receives a heat source 348 therein such as a light bulb, for example, to facilitate a heating of the fragrance in the tray 342. The compartment 346 is formed to militate against a transfer of heat to an outer surface of the main body 312 such as forming the compartment 346 from an insulating material or providing the compartment 346 with reflective walls to cause a transfer of heat to the tray 342, for example.

The main body 312 further includes a fluid reservoir 350. The fluid reservoir 350 receives a fluid (not shown) therein such as water, for example. It is understood that the fluid reservoir 350 has a predetermined fluid capacity. In a non-limiting example, the predetermined fluid capacity is in a range of about 0.1 gallon to about 3 gallons. In another non-limiting example, the predetermined fluid capacity is about 1 gallon. The fluid reservoir 350 is formed from a material which minimizes microbial deterioration of the fluid reservoir 350 and minimizes an amount of and militates against an emergence of impurities such as minerals and pathogens, for example, in the fluid contained therein. In a non-limiting example, the fluid reservoir 350 is formed from a plastic resin material including an antimicrobial additive (e.g. Vinyzene™ SB-1). It is understood, however, that the fluid reservoir 350 can be formed any suitable material. A mouth (not shown) is formed in the fluid reservoir 350 to permit the user to fill the fluid reservoir 350 with the fluid. The mouth is accessible to the user when the discharge vent 324 is separated from the main body 312.

As illustrated, the main body 312 further includes a wishbone shaped fluid level indicator 354. The indicator 354 is formed from a substantially transparent or translucent material to permit the user to monitor a fluid level in the fluid reservoir 350, and determine when the fluid reservoir 350 needs to be refilled. It is understood that the indicator 354 can be any indicator having any shape and size as desired. In the embodiment shown, the fluid reservoir 350 further includes a light source (not shown) disposed therein. The light source illuminates the fluid reservoir 350, thereby causing the indicator 354 to emit light therefrom, in a non-limiting example, the humidifier 300 including the light source acts as a night light.

A base 356 may be provided on the main body 312. The base 356 supports the main body 312, permitting the humidifier 300 to be placed on a substantially planar surface such as a floor, a counter top, or a desktop, for example. It is understood that the base 356 can have any shape and size as desired. The main body 312 may also include human interfaces 360 necessary for operation and control of the humidifier 300. In the embodiment shown, the human interfaces 360 are for activating and deactivating the humidifier 300, the heat source 348, and the light source, and for increasing and decreasing a volume of the mist emitted from the humidifier 300. It is understood that the human interfaces 360 can be used for operating and controlling other components, devices, and features of the humidifier 300 such as activating and deactivating the oscillation mechanism and the heater for heating the mist, for example. Additional or fewer human interfaces 360 than shown for operating and controlling other components, devices, and features of the humidifier 300 can be employed if desired. It is understood that the human interfaces 360 can be located anywhere on the humidifier 300 as desired. It is further understood that the human interfaces 360 can be any human interfaces 360 such as a push button, a rotatable knob, a slide, a toggle switch, and the like, for example.

The main body 312 may also include indicia 362 (e.g. a fluid droplet symbol) or a light source 364 (e.g. a light emitting diode) for indicating a volume level of the mist emitted from the humidifier 300 or activation of the humidifier 300, for example. As illustrated in FIG. 7, the volume level of the mist emitted from the humidifier 300 ranges between a minimum level indicated by one small indicia 362 and a maximum level indicated by one large indicia 362.

In operation, the user separates the discharge vent 324 from the main body 312, thereby providing access to the mouth of the fluid reservoir 350. The fluid reservoir 350 is then filled with the fluid. The discharge vent 324 is then placed on the main body 312 and removeably coupled thereto. While the fluid is the fluid reservoir 350, the antimicrobial additive in the material used to form the fluid reservoir 350 minimizes microbial deterioration of the fluid reservoir 350 caused by the impurities and minimizes the amount of and militates against the emergence of the impurities in the fluid. Particularly, in a non-limiting example, molecules of the antimicrobial additive in the material used to form the fluid reservoir 350 migrate, overtime, from a molecular substrate of the material and onto a surface thereof to form an antimicrobial film thereon. The migration of the antimicrobial molecules is driven by inherent compatibility differences between the antimicrobial molecules and the substrate of the material. The antimicrobial molecules of the antimicrobial film interact with the fluid in the fluid reservoir 350 to minimize the amount of and militate against the emergence of the impurities in the fluid. The antimicrobial film on the surface of the material is replenished by the migration of additional molecules from the substrate.

An initial actuation of one of the human interfaces 360 by the user causes the humidifier 300 to activate. Particularly, the diaphragm disposed in the hollow interior 314 of the main body 312 is caused to vibrate at an ultrasonic frequency. The vibration of the diaphragm generates pressure waves in the fluid gradually released from the fluid reservoir 350. The pressure waves have a desired intensity such that when the pressure waves reach a surface of the fluid above the diaphragm, the pressure waves expel the fluid droplets, creating a mist. The mist travels through the main body 312 of the humidifier 300, into and through the passageway 331 of the discharge vent 324, and through the discharge outlet 332. The cover 334 disperses the fluid droplets of the mist to humidify the surrounding air. When the user desires a concentrated dispersion of the mist, the discharge vent 324 is positioned in the first position. When the user desires to increase the area of the surrounding air into which the mist is emitted, the discharge vent 324 is positioned in the second position as indicated by the dashed lines in FIG. 7. A subsequent actuation of one of the human interfaces 360 by the user causes the humidifier 300 to deactivate. The user monitors the fluid level indicator 354 to determine when the fluid reservoir 350 needs to be refilled.

The user may also actuate other human interfaces 360 to control the volume of the mist emitted from the humidifier 300, and activate and deactivate other features of the humidifier 300 such as the heat source 348 for heating the fragrance in the tray 342, the light source for illuminating the fluid reservoir 350, the oscillation mechanism for causing the discharge vent 324 to oscillate, and the heater for heating the mist, for example.

To fill, remove, or replace the fragrance in the cavity 344 of the tray 342, the cover 334 is separated from the spout 328 of the discharge vent 323. Once the fragrance is filled, removed, or replaced, the cover 334 is placed and secured in the recess 333 thereof.

To insert, remove, or replace the heat source 348 in the compartment 346, the cover 334 and tray 342 are separated from the spout 328 of the discharge vent 324. After the heat source 348 is inserted, removed, or replaced, the tray 342 is placed in the indentation 340 of the spout 328 and the cover 334 is placed and secured in the recess 333 thereof.

From the foregoing description, one ordinarily skilled in the art can easily ascertain the essential characteristics of this invention and, without departing from the spirit and scope thereof, can make various changes and modifications to the invention to adapt it to various usages and conditions.

What is claimed is:

1. A humidifier comprising:
   a main body having a hollow interior, the main body including a fluid reservoir for receiving a fluid therein, wherein the fluid reservoir is formed from a material which at least one of minimizes an amount of impurities in the fluid and militates against an emergence of impurities in the fluid; and
   an extensible discharge vent coupled to the main body and having a neck portion, the vent positionable between a retracted position wherein the neck portion is received in the hollow interior of the main body and an extended position wherein the neck portion extends outward from the main body, wherein in both the retracted position and the extended position the discharge vent emits a mist of the fluid to humidify surrounding air.

2. The humidifier according to claim 1, wherein the main body includes a diaphragm disposed therein, the diaphragm vibratable at an ultrasonic frequency to generate the mist.

3. The humidifier according to claim 1, wherein the fluid reservoir is selectively illuminated by a light source.

4. The humidifier according to claim 1, wherein the fluid reservoir is received in a cavity formed in the main body, the fluid reservoir positionable between an open position and a closed position.

5. The humidifier according to claim 1, wherein the fluid reservoir is formed from a material which minimizes a microbial deterioration of the fluid reservoir.

6. The humidifier according to claim 1, wherein the fluid reservoir is formed from a material including an antimicrobial additive.

7. The humidifier according to claim 1, wherein the main body and the fluid reservoir include an opening formed therein to facilitate at least one of a transportation of the humidifier and a positioning of the fluid reservoir.

8. The humidifier according to claim 1, further comprising an oscillation mechanism coupled to the discharge vent to cause an oscillation of the discharge vent when the discharge vent is in the extended position.

9. The humidifier according to claim 8, wherein the oscillation mechanism is automatically activated when the discharge vent is in the extended position and automatically deactivated when the discharge vent is in the retracted position.

10. The humidifier according to claim 1, wherein the discharge vent includes a removable tray for receiving a fragrance therein.

11. The humidifier according to claim 10, wherein the discharge vent includes a compartment for receiving a heat source for heating the fragrance disposed in the tray.

12. A humidifier comprising:
    a main body having a hollow interior, the main body including a fluid reservoir for receiving a fluid therein, wherein the fluid reservoir is formed from a material which minimizes an amount of impurities in the fluid and a microbial deterioration of the fluid reservoir, and militates against an emergence of impurities in the fluid;
    an extensible discharge vent coupled to the main body, the discharge vent selectively positionable between a retracted position and an extended position, wherein the discharge vent emits a mist of the fluid to humidify surrounding air; and
    an oscillation mechanism coupled to the discharge vent to cause an oscillation of the discharge vent when the discharge vent is in the extended position.

13. The humidifier according to claim 12, wherein the fluid reservoir is selectively illuminated by a light source disposed in the main body.

14. The humidifier according to claim 12, wherein the oscillation mechanism is automatically activated when the discharge vent is in the extended position and automatically deactivated when the discharge vent is in the retracted position.

15. The humidifier according to claim 12, wherein the discharge vent includes a removable tray for receiving a fragrance therein.

16. The humidifier according to claim 15, wherein the discharge vent includes a compartment for receiving a heat source for heating the fragrance disposed in the tray.

17. The humidifier according to claim 12, wherein the vent includes a neck portion, and in the retracted position the neck portion is received in the hollow interior of the main body, and in the extended position the neck portion extends outward from the main body.

18. The humidifier according to claim 12, wherein the main body includes a diaphragm disposed therein, the diaphragm vibratable at an ultrasonic frequency to generate the mist.

19. A humidifier comprising:
    a main body having a hollow interior, the main body including a fluid reservoir for receiving a fluid therein, wherein the fluid reservoir is formed from a material which minimizes an amount of impurities in the fluid and a microbial deterioration of the fluid reservoir, and militates against an emergence of impurities in the fluid;
    an extensible discharge vent coupled to the main body, the discharge vent selectively positionable between a retracted position and an extended position, wherein the discharge vent emits a mist of the fluid to humidify surrounding air; and
    an oscillation mechanism coupled to the discharge vent to cause an oscillation of the discharge vent when the discharge vent is in the extended position, wherein the oscillation mechanism is automatically activated when the discharge vent is in the extended position and automatically deactivated when the discharge vent is in the retracted position.

20. The humidifier according to claim 19, wherein the vent includes a neck portion, and in the retracted position the neck portion is received in the hollow interior of the main body, and in the extended position the neck portion extends outward from the main body.

* * * * *